United States Patent
Itoh et al.

(10) Patent No.: US 8,836,052 B2
(45) Date of Patent: Sep. 16, 2014

(54) ELECTROMECHANICAL TRANSDUCER AND METHOD OF MANUFACTURING THE SAME

(75) Inventors: Hideyuki Itoh, Machida (JP); Takahiro Ezaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 402 days.

(21) Appl. No.: 12/956,046

(22) Filed: Nov. 30, 2010

(65) Prior Publication Data

US 2011/0140212 A1 Jun. 16, 2011

(30) Foreign Application Priority Data

Dec. 16, 2009 (JP) ................. 2009-284625

(51) Int. Cl.
*H01L 27/14* (2006.01)
(52) U.S. Cl.
USPC ........... 257/414; 257/415; 257/416; 257/417; 257/418; 257/419; 257/420
(58) Field of Classification Search
USPC ................. 257/E29.324, 414–420; 367/181; 438/455–459
See application file for complete search history.

(56) References Cited

U.S. PATENT DOCUMENTS

| | | | |
|---|---|---|---|
| 6,114,798 A | 9/2000 | Maruyama et al. | |
| 6,291,932 B1 | 9/2001 | Maruyama et al. | |
| 6,668,437 B1 | 12/2003 | Maruyama et al. | |
| 6,951,048 B2 | 10/2005 | Maruyama et al. | |
| 2001/0004550 A1* | 6/2001 | Passemard | 438/618 |
| 2005/0017313 A1* | 1/2005 | Wan | 257/415 |
| 2006/0075818 A1 | 4/2006 | Huang et al. | |
| 2006/0115382 A1 | 6/2006 | Ezaki et al. | |
| 2007/0013269 A1* | 1/2007 | Huang | 310/334 |
| 2008/0048211 A1* | 2/2008 | Khuri-Yakub et al. | 257/204 |
| 2008/0197751 A1* | 8/2008 | Huang | 310/311 |
| 2009/0169035 A1* | 7/2009 | Rombach et al. | 381/175 |
| 2011/0018387 A1* | 1/2011 | Ogawa et al. | 310/300 |
| 2011/0073968 A1* | 3/2011 | Ezaki et al. | 257/416 |

FOREIGN PATENT DOCUMENTS

WO 2010/002009 A2 1/2010

* cited by examiner

*Primary Examiner* — Jae Lee

(74) *Attorney, Agent, or Firm* — Fitzpatrick, Cella, Harper & Scinto

(57) ABSTRACT

An electromechanical transducer includes multiple elements each having multiple cells, with each cell including a first electrode formed from a conductive substrate, and a second electrode opposed to a first face of the conductive substrate and across a gap. The multiple cells of each of the elements are electrically connected, and the conductive substrate is divided for each of the elements by grooves extending from the first face to a second face which is opposite from the first face. In addition, insulating films are formed on opposing side walls of the conductive substrate and define each of the grooves, wherein a gap width of each of the grooves is narrower on the second face side of the conductive substrate than on the first face side of the conductive substrate.

7 Claims, 2 Drawing Sheets

ELECTROMECHANICAL TRANSDUCER AND METHOD OF MANUFACTURING THE SAME

BACKGROUND OF THE INVENTION

1. Field of the Invention

The present invention relates to an electromechanical transducer such as an ultrasonic transducer, and to a method of manufacturing the electromechanical transducer. More specifically, the present invention relates to a technology of improving the reliability of an electromechanical transducer.

2. Description of the Related Art

Ultrasonic transducers perform conversion from an electrical signal to an ultrasonic wave and conversion from an ultrasonic wave to an electrical signal, and are used, among others, as probes for medical imaging or non-destructive inspection. One form of ultrasonic transducer is a capacitive micromachined ultrasound transducer (CMUT). A CMUT generally includes a substrate, which has a lower electrode, a membrane, which is supported to the substrate by a supporting portion formed on the substrate, and an upper electrode. The CMUT uses a voltage applied between the lower electrode and the upper electrode to cause the membrane to vibrate and emit ultrasonic waves. The CMUT also receives ultrasonic waves which cause the membrane to vibrate and, from the resultant change in the capacitance between the lower electrode and the upper electrode, detects the ultrasonic waves.

Conventionally, CMUTs have been manufactured with the use of surface micromachining, bulk micromachining, or the like. The conventional CMUT manufacture may employ a wiring method in which at least one combination of a membrane and a cavity (namely, at least one cell) on a silicon substrate constitutes a single element, and the element is connected to a circuit board, with the silicon substrate itself acting as a lower electrode and as electrical through-wafer interconnects. In a known example of this wiring method, elements of a CMUT are two-dimensionally arranged into arrays by providing a groove that separates the lower electrode of one element from the lower electrode of another element to electrically isolate the elements from one another, and then leading their respective wirings out from the back (see U.S. Patent No. 2006/0075818 A1 and U.S. Patent No. 2007/0013269 A1). In another known method, a high level of insulation between adjacent elements is obtained by filling the groove with an insulating substance such as epoxy resin.

However, with a conventional CMUT that has a groove for separating one lower electrode from another as described above, there is a possibility of a conductive foreign object entering the groove during the manufacture process or while the CMUT is in use, and bridging the lower electrodes adjoined to the groove to cause a short circuit.

SUMMARY OF THE INVENTION

In view of the above-mentioned problem, an electromechanical transducer according to the present invention includes: multiple elements each including at least one cell including a first electrode, which is formed from a conductive substrate, and a second electrode, which is opposed to a first face of the conductive substrate across gaps; grooves piercing the conductive substrate from the first face to a second face, which is opposite from the first face, to divide the conductive substrate into sections allocated to the multiple elements; and insulating films formed on opposing outer side walls of every two adjacent conductive substrate sections across one of the grooves. A width between the insulating films sandwiching the one of the grooves is narrower on the second face side of the conductive substrate than on the first face side of the conductive substrate, and the insulating films sandwiching the one of the grooves are thicker on the second face side of the conductive substrate than on the first face side of the conductive substrate.

Further, in view of the above-mentioned problem, an electromechanical transducer manufacturing method according to the present invention is a method of manufacturing an electromechanical transducer, which includes multiple elements each including at least one cell in which a conductive substrate is provided as first electrodes and a second electrode is opposed to a first face of the conductive substrate across gaps, the electromechanical transducer manufacturing method including: forming grooves in the conductive substrate to form the first electrodes for each of the multiple elements; and forming insulating films on opposing outer side walls of every two of the first electrodes that are adjacent across one of the grooves, in a manner that makes the insulating films thicker on a second face side of the conductive substrate than on the first face side of the conductive substrate, the first face of the conductive substrate being a face on which the multiple elements are disposed, the second face of the conductive substrate being opposite from the first face, and in a manner that makes a width between the insulating films sandwiching the one of the grooves is narrower on the second face side of the conductive substrate than on the first face side of the conductive substrate.

According to the present invention, where the outer side walls of the first electrodes separated from one another by the grooves are covered with the insulating films, a foreign object entering one of the grooves which are gaps is prevented from causing a short circuit between the first electrodes adjoined to the groove. In addition, the width between the insulating films on the opposing outer side walls of every two adjacent first electrodes is narrower on the groove opening side (i.e., the side of the second face of the substrate which is opposite from the first face of the substrate) than on the groove bottom side (i.e., the side of the first face of the substrate). This means that a foreign object that manages to enter the groove is smaller than the width of a deeper part of the groove away from the opening (the groove bottom width), and does not span the distance between the opposing outer side walls of the adjacent first electrodes. Consequently, a higher inter-electrode insulation effect is expected and the electromechanical transducer is improved in reliability.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Embodiments of the present invention are described below. An important point of an electromechanical transducer according to the present invention is that insulating films are formed on outer side walls of first electrodes, which are formed by cutting grooves in a substrate, such that the width between every two insulating films sandwiching one of the grooves is narrower on the side of a second face of the substrate than on the side of a first face of the substrate, the first face of the substrate being where elements are disposed, the second face of the substrate being opposite from the first face of the substrate. Another important point is that insulating films are formed on opposing outer side walls of every two adjacent first electrodes across one of the grooves in a manner that makes the insulating films thicker on the side of the second face of the substrate than on the side of the opposite first face of the substrate.

Based on this concept, basic modes of an electromechanical transducer according to the present invention and an electromechanical transducer manufacturing method according to the present invention are structured as described in "Summary of the Invention." The basic modes can be developed into the following embodiments. For instance, the substrate, from which the first electrodes (lower electrodes to be described later) are formed, may be made of silicon, and the insulating films may be thermal oxide films (see a first embodiment described below). The elements may be capacitive electromechanical conversion elements (see the first embodiment described below). The grooves may be, for example, ones formed by dry etching such as Deep RIE, or ones formed in a silicon substrate by alkaline wet etching. The first electrodes are connected to a circuit board directly, or via a relay substrate which has electrical through-hole-wafer interconnects. The embodiments are now described with reference to the drawings.

First Embodiment

The first embodiment deals with a capacitive micromachined ultrasound transducer (CMUT) as an electromechanical transducer to which the present invention can be applied. However, the present invention is applicable not only to CMUTs but also to any electromechanical transducers that have a similar structure (a structure in which a substrate is divided by grooves to form first electrodes of the respective elements). For example, the present invention is applicable to ultrasonic transducers that use distortion, a magnetic field, or light (piezoelectric micromachined ultrasound transducers (PMUTs), magnetic micromachined ultrasound transducers (MMUTs), and the like). In other words, electromechanical transducers to which the present invention can be applied are not limited to those whose lower electrodes 103 (first electrodes) to be described later are structured as below.

Figure 1:
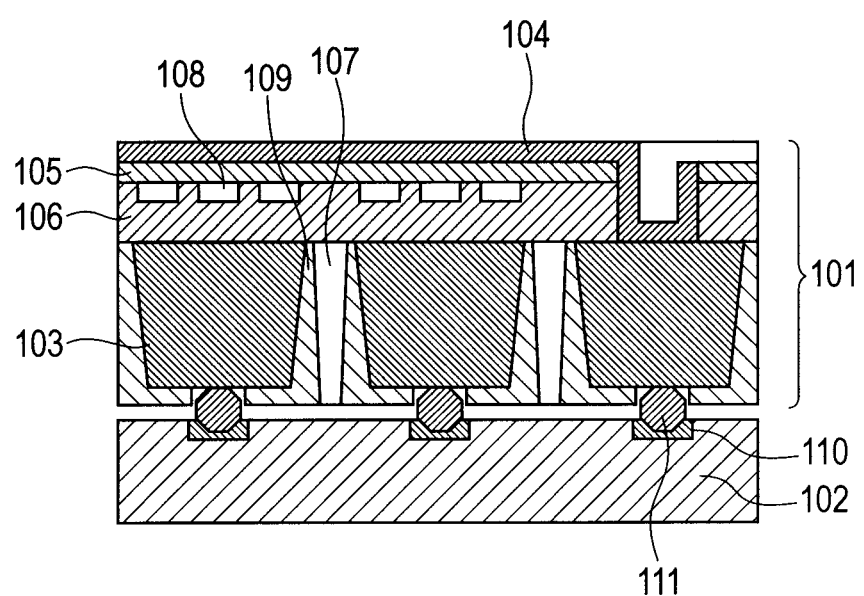
FIG. 1 is a sectional view of a capacitive micromachined ultrasound transducer (CMUT) given as an example of an electromechanical transducer to which the present invention can be applied.

As illustrated in FIG. 1, which is a schematic diagram illustrating the sectional structure of the CMUT of this embodiment, an element substrate 101 of the CMUT of this embodiment is electrically connected to a circuit board 102. The element substrate 101 and the circuit board 102 are fixed to each other, with the circuit board 102 placed under the element substrate 101. Elements each having multiple cells are two-dimensionally arranged on the element substrate 101. Each cell includes an upper electrode 104, which is a second electrode, a membrane 105, a supporting portion 106, which is made from an insulator, and one lower electrode 103, which is the first electrode. Cavities 108 which are gaps are formed between the upper electrode 104 and the lower electrode 103. The lower electrode 103 of one element is separated from the lower electrode 103 of another element by forming grooves 107, which pierce the conductive electrode substrate from the second face described above to the first face described above in the thickness direction. In this embodiment, opposing outer side wall surfaces of every two adjacent lower electrodes 103 across one of the grooves 107 are covered with insulating films 109. The outer side walls of the lower electrodes 103 are lower electrode surfaces newly exposed along the grooves 107 by forming the grooves 107 in the conductive electrode substrate. The width between the insulating films 109 on the opposing outer side wall surfaces of the adjacent lower electrodes 103 across the groove 107 becomes narrower from the side of the first face of the substrate which is the bottom side of the groove 107 toward the side of the circuit board 102 (the side of the second face of the substrate which is the opening side of the groove 107). The interior of each groove 107 is a gap and is not filled with an insulating substance or any other substances.

In each element, the cavities 108 of multiple cells may be sealed and independent of one another, or may communicate with one another. Multiple cells are electrically connected in parallel to constitute an element. Each element needs to include at least one cell, but the number of cells in each element, cell arrangement, the form of the cavities 108, and other similar aspects are set freely as long as the function of electromechanical transduction is implementable. The arrangement and number of elements, too, are not limited to those of this embodiment, and as many elements as desired can be provided and arranged in a desired manner. The grooves 107 take a form suitable for the employed element arrangement or the like. The upper electrode may double as the membrane. The circuit board 102 includes a processing circuit (not shown) for processing signals and electrode pads 110, which are electrically connected to the lower electrodes 103 by solder bumps 111.

The CMUT structured as above operates, for example, in the following manner. When ultrasonic waves are received, the membrane 105 is displaced and the displacement changes the gap between the upper electrode 104 and the lower electrode 103 in a cell. The resultant change in capacitance is detected by the signal processing circuit of the circuit board 102, where signal processing is performed to obtain an ultrasonic image. To transmit ultrasonic waves, a voltage is applied from the circuit board 102 to the upper electrode 104 or the lower electrode 103, thereby causing the membrane 105 to vibrate and emit ultrasonic waves. The CMUT of this embodiment can be manufactured by a bonding type method (bulk micromachining), a surface type method (surface micromachining), or the like. In the bonding type method, for example, cavities are formed in a silicon substrate and then an SOI substrate is bonded to form a membrane (see a second embodiment described below). In the surface type method, a membrane is formed on a sacrificial layer, which is subsequently etched away through etching holes formed in the membrane, and lastly the etching holes are filled with a silicon nitride film or the like to form cavities.

The lower electrodes 103 and the insulating films 109 on the outer side walls of the lower electrodes 103 in this embodiment are described next in detail. The width (distance) between every two insulating films 109 sandwiching one of the grooves 107, which separate the lower electrodes 103 from one another, becomes narrower toward the opening side of the groove 107 and, when inner side walls of the groove 107 which are constituted of the insulating films 109 have a wider gradient angle with respect to the substrate 101, a better effect is obtained. This makes the width of the groove 107 between the insulating films 109 wider at the bottom than at the opening, with the result that a particulate foreign object entering the groove 107 cannot bridge the opposing outer side walls of the adjacent lower electrodes 103. More desirably, in addition to covering the outer side walls of the lower electrodes 103, the insulating films 109 are formed on the bottom faces of the lower electrodes 103 where the lower electrodes 103 are bonded to the circuit board 102, except for portions for wiring led to the circuit board 102. This way, a short circuit is prevented even if a thin, linear, foreign object intrudes and connects two adjacent lower electrodes 103 to each other.

It is preferred that the lower electrodes 103 used in this embodiment be formed from a semiconductor substrate that is easy to micromachine, such as a silicon substrate. It is preferred that the resistivity of the lower electrodes 103 be less than 0.02 Ω·cm. This is because a lower wiring resistance of the lower electrodes 103 means a small signal loss. Thinner lower electrodes 103 equal a smaller parasitic capacitance between two adjacent lower electrodes 103, and equal a lower wiring resistance. It is therefore preferred that the thickness of the lower electrodes 103 be 100 μm or less. It is preferred that the insulating films 109 formed on the outer side walls of the lower electrodes 103 be silicon thermal oxide films. This is because an oxide film has little chance of particles or other foreign objects mixing in owing to how the film is processed, and does not require ensuring that the adhesion is strong enough to prevent the film from peeling off. Another advantage of employing an oxide film is that, when the lower electrodes 103 are thermally oxidized after the grooves 107 which separate the lower electrodes 103 from one another are formed in, for example, a direction perpendicular to the substrate surface, oxide films thicker toward the opening side of the grooves 107 are formed on the surfaces of the lower electrodes 103, and facilitates the building of the device structure in which the distance between the insulating films 109 formed on the outer side walls of every two adjacent lower electrodes 103 is narrower toward the groove opening side. In this case, in building the groove structure that is narrower on the opening side, the width of the grooves 107 at the bottom which is on the first face side does not need to be so wide if the grooves 107 separating the lower electrodes 103 are formed to have a vertical shape, and the isolation width between elements can therefore be narrowed. With the element isolation width narrowed, the number of cavities 108, which cannot be disposed in places where the grooves 107 are formed, can be increased per unit area of the substrate 101, and the overall sensitivity of the devices is enhanced (the fill factor is increased).

When the insulating films 109 are formed by thermal oxidation, it is preferred that the width of the grooves 107 be narrow in order to prevent foreign objects from entering the grooves 107. A high aspect ratio is also preferred because then a gradient is created in the concentration of oxygen gas which diffuses in the depth direction of the grooves 107 during thermal oxidation, thereby making formed oxide films thicker toward the groove opening side. The depth of the grooves 107 depends on the thickness of the lower electrodes 103. The groove width that satisfies this condition is therefore desirably 5 μm or less, more desirably, 3 μm or less. It is preferred that the thermal oxide films 109 in this embodiment be thicker on the groove opening side to make each groove 107 that determines the distance between two adjacent lower electrodes 103 narrower on the groove opening side. It is preferred that the inner side walls (the thermal oxide films 109) of the groove 107 each have a thickness of 0.4 to 0.5 μm on the bottom side and a thickness of 1 μm or more on the opening side. Note that the thicknesses given here slightly vary depending on oxidation conditions.

On the surfaces of lower electrodes which are separated from one another by grooves structured as above, insulating films are formed thicker toward the openings of the grooves. Foreign objects are thus prevented from entering the grooves. Even if a foreign object enters one of the grooves, because the width of the groove which is the distance between the opposing insulating films across the groove is wider in a deeper part of the groove away from the opening (wider on the groove bottom side than on the groove opening side), the foreign object cannot bridge the adjacent lower electrodes, at least when the foreign object is a particle. The expected short-circuit preventing effect is therefore higher than in prior art.

Second Embodiment

The second embodiment deals with a method of manufacturing a CMUT as an electromechanical transducer to which the present invention can be applied. According to the manufacturing method of this embodiment, a CMUT is manufactured as follows. A Si substrate is prepared in which grooves separate lower electrodes of respective elements from one another, and insulating films are formed on lower electrode surfaces that face the grooves. An SOI substrate is bonded onto the Si substrate to form a membrane, and the lower electrodes are wired to a circuit board. The insulating films on the outer side walls of the lower electrodes separated from one another by the grooves are formed by thermal oxidation.

By thermally oxidizing the lower electrodes, oxide films are formed on the outer side walls of the lower electrodes to be thicker toward the groove opening side, and a device form in which the groove width is narrower toward the groove opening side is obtained easily. An oxide film has little chance of particles or other foreign objects mixing in owing to how the film is processed, and does not require ensuring that the adhesion is strong enough to prevent the film from peeling off. Another advantage of employing an oxide film is that oxide films are formed on the bottom faces of the lower electrodes at the same time the outer side walls of the lower electrodes are covered with oxide films, thereby insulating other portions of the lower electrodes at the same time as their outer side walls. However, in order to wire the lower electrodes to the circuit board, electrical continuity needs to be secured by not oxidizing the bottom faces of the lower electrodes entirely or partially. In this embodiment, regions where electrical continuity from the lower electrodes needs to be secured are covered with a SiN film before the insulating films are formed. The insulating films are then formed by thermal oxidation and, lastly, the SiN film is removed to secure electrical continuity of the lower electrodes. The Si substrate prepared first later forms the lower electrodes and is therefore preferred to have a low resistivity. In this embodiment, a Si substrate having a specific resistance less than 0.02 Ω·cm is used. The thickness of the Si substrate used should be 100 μm or more and 525 μm or less.

Figure 2A:
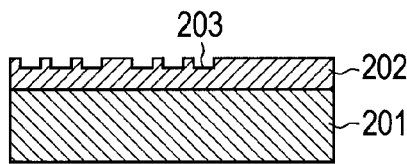
FIGS. 2A, 2B, 2C, 2D, 2E, 2F, 2G, 2H and 2I are diagrams illustrating the process flow of a CMUT manufacturing method according to a second embodiment of the present invention.

FIGS. 2A to 2I illustrate the process flow of this embodiment. First, a Si substrate 201 is thermally oxidized to form an oxide film 202. Next, a resist pattern for a cavity pattern is formed by photolithography. Buffered hydrofluoric acid (BHF) is used to etch the oxide film 202 with the resist pattern as a mask, thereby forming concave portions 203 for cavities. FIG. 2A is a sectional view of the Si substrate 201 after the concave portions 203 for cavities are formed. Next, the Si substrate is thermally oxidized again in order to insulate the bottom faces of the cavities.

Figure 2F:
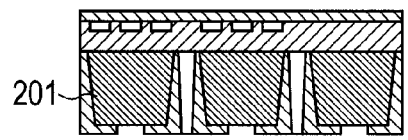
Figure 2B:
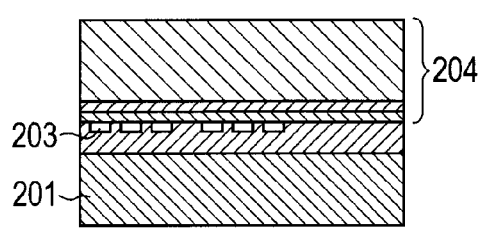
Figure 2G:
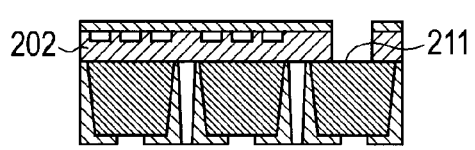
Figure 2C:
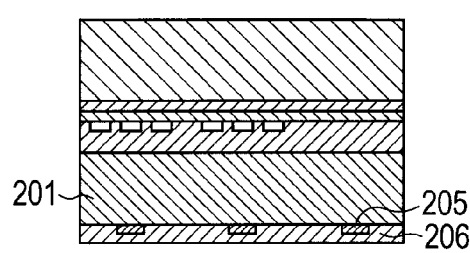

The surface of the Si substrate 201 where the concave portions 203 for cavities have been formed and the surface of an SOI substrate 204 are washed and subjected to surface activation treatment, and the substrates are then bonded to each other in vacuum. The cavities are formed through this step. FIG. 2B is a sectional view of the substrates after the wafer bonding. Next, a groove pattern for separating a lower electrode of one element from a lower electrode of another element and a lower electrode lead-out wiring pattern are formed by photolithography on the bottom of the Si substrate 201. To secure the wiring pattern for establishing electrical continuity from the lower electrodes to a circuit board, a SiN film is formed first on the bottom of the Si substrate 201. Photolithography is performed to form the wiring pattern from a resist. The SiN film is then etched with the resist pattern as a mask, and the resist is subsequently removed. To form the grooves between the lower electrodes next, a Cr film 206 is formed on the Si substrate 201, where the SiN pattern, denoted by 205, still remains. FIG. 2C is a sectional view of the substrates after the Cr film is formed.

Figure 2H:
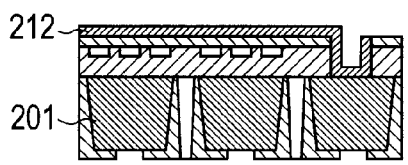
Figure 2D:
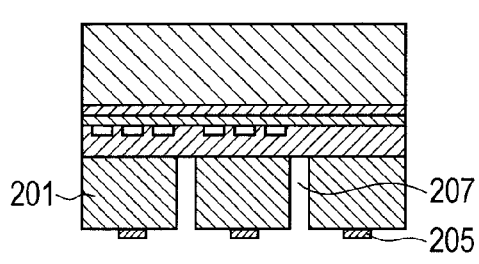

The groove pattern is formed from a resist by photolithography. With the resist pattern as a mask, the Cr film is etched and the resist is subsequently removed. The remaining Cr pattern is used as a mask in the dry etching of the Si substrate 201, thereby forming grooves 207. The grooves 207 are formed to have a vertical shape by Deep RIE or the like. Through this step, lower electrodes are separated from one another on an element basis. After the grooves 207 are formed, the Cr film is removed. FIG. 2D is a sectional view of the substrates after the formation of the grooves 207.

Figure 2I:
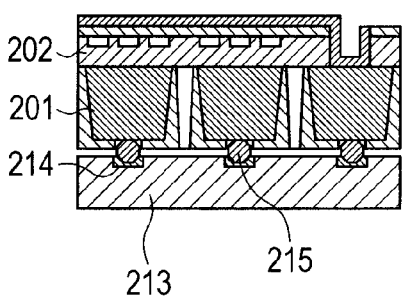
Figure 2E:
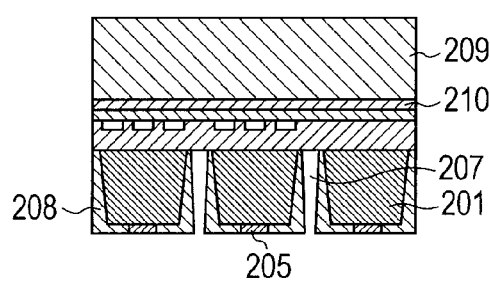

To form an oxide film 208 on the outer side walls of the lower electrodes which have undergone the formation of the grooves 207, the Si substrate 201 is thermally oxidized once more. In this step, the regions where the SiN pattern 205 remains are not oxidized. FIG. 2E is a sectional view of the substrates after the thermal oxidation of the substrate 201. During the thermal oxidation, a gradient in oxygen concentration is created in the depth direction of the grooves 207 and, as a result, the oxide film 208 is formed on the outer side walls of the lower electrodes to be thicker toward the groove opening side. Therefore, a preferred condition of the thermal oxidation creates a thickness gradient in which the thickness of the oxide film 208 formed on the outer side walls of the lower electrodes increases along the depth direction of the grooves 207. The thermal oxidation is conducted at a temperature of 1,000° C. to 1,100° C. while maintaining the oxygen concentration gradient. Through this step, the oxide film 208 is formed thicker toward the groove opening side, and the grooves 207 which have had a vertical shape are narrowed toward the opening side. The oxide film 208 is formed inside the Si substrate 201 as well as on the surface of the Si substrate 201, and now has a sectional shape illustrated in FIG. 2E. The groove openings may be partially closed accidentally, which does not cause a problem. The SiN pattern 205 is removed after the oxide film 208 is formed.

Next, a supporting substrate layer 209 and an embedded oxide layer 210 are removed by etching from the SOI substrate 204. Through this step, a membrane is formed. FIG. 2F is a sectional view of the substrates after the membrane is formed. The process steps subsequent to the formation of the grooves 207 may include suitable reinforcement measures if the device strength is determined to be insufficient. An upper electrode lead-out wiring forming portion 211 is formed next. A resist pattern for the upper electrode lead-out wiring forming portion 211 is formed on the membrane by photolithography. With the resist pattern as a mask, the membrane and a supporting portion constituted of the oxide film 202 are etched. FIG. 2G is a sectional view of the substrates after the upper electrode lead-out wiring forming portion 211 is formed.

Next, Al is deposited by evaporation in the upper electrode lead-out wiring forming portion 211 to form an Al film 212. On the face where Al is deposited by evaporation, a resist pattern for upper electrodes is formed by photolithography. With the resist pattern as a mask, the Al film 212 is subjected to wet etching to form the upper electrodes. FIG. 2H is a sectional view of the substrates after the formation of the upper electrodes. Lastly, the lower electrodes denoted by 201 are positioned with respect to electrode pads 214 of the circuit board denoted by 213, and the two substrates are bonded to each other by solder bumps 215. A CMUT capable of signal processing for ultrasound transmission and reception is thus manufactured. FIG. 2I is a sectional view of the CMUT completed by the process of this embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-284625, filed Dec. 16, 2009, which is hereby incorporated by reference herein in its entirety.

What is claimed is:

1. An electromechanical transducer, comprising:
multiple elements each comprising at least one cell, each of the elements including:
a first electrode, and
a second electrode opposed to a first face of the first electrode so as to interpose a cavity between the first electrode and the second electrode,
wherein the first electrode comprises a conductive substrate that is divided for each of the elements by grooves extending from the first face to a second face which is opposite from the first face; and
insulating films formed on opposing side walls of the conductive substrate and defining each of the grooves,
wherein a width of each of the grooves is narrower on the second face side of the conductive substrate than on the first face side of the conductive substrate, and
wherein the cavity and the grooves are not connected to each other.

2. The electromechanical transducer according to claim 1, wherein the conductive substrate comprises silicon, and the insulating films are formed from thermal oxide films.

3. The electromechanical transducer according to claim 1, wherein the multiple elements are capacitive electromechanical conversion elements.

4. The electromechanical transducer according to claim 1, wherein the insulating films defining each of the grooves are thicker on the second face side of the conductive substrate than on the first face side of the conductive substrate.

5. The electromechanical transducer according to claim 1, wherein each portion of the substrate divided for each of the elements is larger in width on the first face side of the conductive substrate than on the second face side of the conductive substrate.

6. The electromechanical transducer according to claim 1, wherein the grooves are not closed by the insulating films.

7. The electromechanical transducer according to claim 1, wherein the first electrode and the second electrode are applied with a voltage when transmitting or receiving an ultrasonic wave.

* * * * *